US00PP34932P2

(12) United States Plant Patent
Heuger

(10) Patent No.: US PP34,932 P2
(45) Date of Patent: Jan. 17, 2023

(54) ***HELLEBORUS* PLANT NAMED 'HL 1010'**

(50) Latin Name: ***Helleborus* x *lemperii* (*Helleborus niger* X *Helleborus* x *hybridus*)**
Varietal Denomination: HL 1010

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/863,111

(22) Filed: Jul. 12, 2022

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

(56) References Cited

PUBLICATIONS

Northwest Perennial Alliance website citation for HGC Leona. https://www.northwestperennialalliance.org/Sys/Store/Products/270786. accessed Aug. 1, 2022. 1 page. (Year: 2022).*

* cited by examiner

*Primary Examiner* — Karen M Redden
(74) *Attorney, Agent, or Firm* — C. Anne Whealy

(57) ABSTRACT

A new and distinct cultivar of *Helleborus* plant named 'HL 1010', characterized by its upright to somewhat outwardly spreading and mounded plant habit; moderately vigorous to vigorous growth habit; dark green-colored leaves; freely flowering habit; purplish red-colored flowers; and good garden performance.

2 Drawing Sheets

Figure 1:
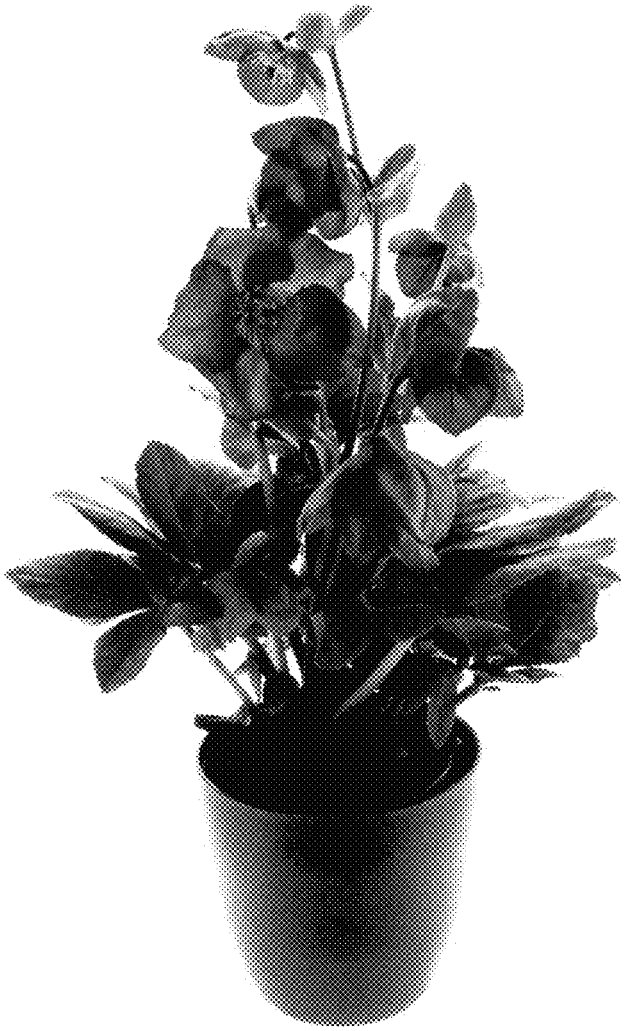

Botanical designation: *Helleborus* x *lemperii* (*Helleborus niger* X *Helleborus* x *hybridus*).
Cultivar denomination: 'HL 1010'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2021, application number 2021/3088. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *lemperii* (*Helleborus niger* X *Helleborus* x *hybridus*) and hereinafter referred to by the name 'HL 1010'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2015 of a proprietary selection of *Helleborus* x *lemperii* identified as code number 2014-1423, not patented, as the female, or seed, parent and a proprietary selection of *Helleborus* x *lemperii* identified as code number 2014-0384, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2016.

Asexual reproduction of the new *Helleborus* plant by in vitro axillary meristem culture in a controlled environment in Glandorf, Germany since March, 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1010'. These characteristics in combination distinguish 'HL 1010' as a new and distinct *Helleborus* plant:

1. Upright to somewhat outwardly spreading and mounded plant habit.
2. Moderately vigorous to vigorous growth habit.
3. Dark green-colored leaves.
4. Freely flowering habit.
5. Purplish red-colored flowers.
6. Good garden performance.

Plants of the new *Helleborus* differ from plants of the female parent selection in the following characteristics:

1. Leaves of plants of the new *Helleborus* are darker green in color than leaves of plants of the female parent selection.
2. Flowers of plants of the new *Helleborus* are purplish red in color whereas flowers of plants of the female parent selection are white in color.

Plants of the new *Helleborus* differ from plants of the male parent selection in the following characteristics:

1. Leaves of plants of the new *Helleborus* are darker green in color than leaves of plants of the male parent selection.
2. Flowers of plants of the new *Helleborus* are purplish red in color whereas flowers of plants of the male parent selection are red in color.

Plants of the new *Helleborus* can also be compared to plants of *Helleborus* x *lemperii* 'HGC Liara', not patented. In side-by-side comparisons, plants of the new *Helleborus* differ primarily from plants of 'HGC Liara' in flower color as flowers of plants of the new *Helleborus* are purplish red in color whereas flowers of plants of 'HGC Liara' are light and dark pink in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1010' grown in a container.

Figure 2:
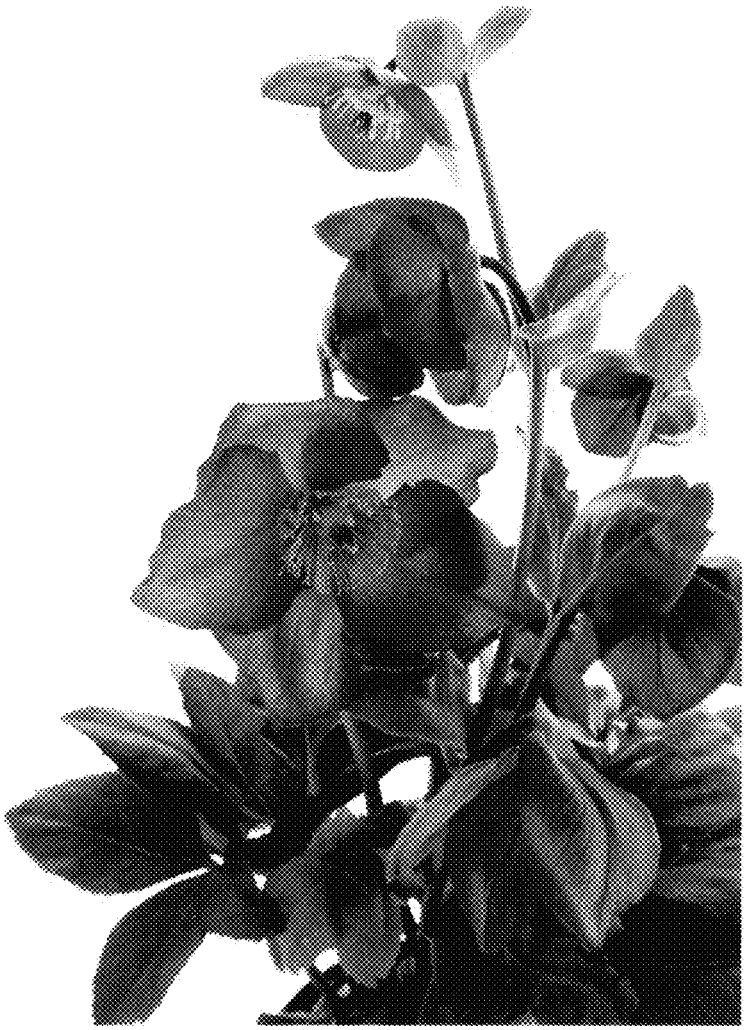

The photograph on the second sheet (FIG.2) is a close-up view of a typical flowering plant of 'HL 1010'.

DETAILED BOTANICAL DESCRIPTION

The aforementioned photographs and following observations, measurements and values describe plants grown during late autumn and early winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *lemperii* (*Helleborus niger* X *Helleborus* x *hybridus*) 'HL 1010'.

Parentage:

*Female, or seed, parent*.—Proprietary selection of *Helleborus* x *lemperii* identified as code number 2014-1423, not patented.

*Male, or pollen, parent*.—Proprietary selection of *Helleborus* x *lemperii* identified as code number 2014-0384, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within and above the foliar plane; plant shape, broad inverted triangular; moderately vigorous to vigorous growth habit and moderate growth rate.

*Plant height, soil level to top of foliar plane*.—About 27.4 cm.

*Plant height, soil level to top of flowers*.—About 38.5 cm.

*Plant diameter* (*area of spread*).—About 43.7 cm.

Leaf description:

*Arrangement*.—Leaves arranged in a basal rosette; leaves palmately compound with typically seven leaflets per leaf.

*Leaf length*.—About 20.8 cm.

*Leaf width*.—About 23.3 cm.

*Leaflet length*.—About 11 cm.

*Leaflet width*.—About 5.8 cm.

*Leaf shape*.—Palmate; roughly reniform in outline.

*Leaflet shape*.—Obovate.

*Leaflet apex*.—Acute to broadly acute.

*Leaflet base*.—Attenuate.

*Leaflet margin*.—Serrate; slightly and coarsely undulate.

*Leaflet texture and luster, upper and lower surfaces*.—Smooth, glabrous; moderately coriaceous; slightly glossy.

*Leaflet venation pattern*.—Pinnate.

*Leaflet color*.—Developing leaflets, upper surface: Close to 138A; towards the base, close to 183A. Developing leaflets, lower surface: Close to 144A. Fully developed leaflets, upper surface: Darker than a blend of 147A and N189A; towards the base, tinged with close to N186C; venation, close to 144A to 144B. Fully developed leaflets, lower surface: Close to 147B; venation, close to 146D.

*Petioles*.—Length: About 14.1 cm. Diameter: About 7 mm by 8 mm. Strength: Strong. Texture and luster, upper and lower surfaces: Smooth, glabrous; moderately glossy. Color, upper and lower surfaces: Close to 146C moderately covered with fine dots, close to N186C.

Flower description:

*Flower shape and habit*.—Single rotate bowl-shaped flowers arranged in panicles; freely flowering habit with numerous flowers developing per plant during the flowering season; flowers face mostly outwardly to nodding.

*Fragrance*.—None detected.

*Natural flowering season*.—Plants begin flowering about ten months after planting; plants flower naturally from late fall into the winter in Germany.

*Flower longevity on the plant*.—About ten days; sepals persistent, other flower parts are not persistent.

*Flower buds*.—Length: About 3.2 cm. Diameter: About 2.2 cm. Shape: Elliptic to obovate. Texture and luster: Smooth, glabrous; matte. Color: Close to 70A; towards the apex, strongly tinged with close to 59A; venation, close to N79C.

*Inflorescence height* (*including peduncle*).—About 35.8 cm.

*Inflorescence diameter*.—About 18.1 cm.

*Flower diameter*.—About 8.3 cm by 8.3 cm.

*Flower depth*.—About 3.2 cm.

*Petals*.—All petals are transformed into nectaries.

*Sepals*.—Quantity and arrangement: About five, arranged in a single whorl. Length: About 5.6 cm. Width: About 4.6 cm. Shape: Broadly ovate, slightly concave. Apex: Bluntly acute. Base: Truncate to rounded. Margin: Entire; slightly to moderately undulate. Texture and luster, upper surface: Smooth, glabrous; matte. Texture and luster, lower surface: Smooth, glabrous; matte to slightly glossy. Color: When opening, upper surface: Close to 71A; towards the base, close to 144B. When opening, lower surface: Close to 59A; towards the base, close to 59B. Fully opened, upper surface: Close to a blend of 71A and 72A; towards the base, close to 75C and at the base, close to 145B to 145C; venation, similar to lamina colors; color does not change with subsequent development. Fully opened, lower surface: Close to 59A to 59B; towards the base, close to 70C; venation, close to 71A; color does not change with subsequent development.

*Flower bracts*.—Quantity per flower: Typically one or two. Length: About 5.5 cm. Width: About 5.2 cm. Shape: Broadly ovate. Apex: Acute. Base: Truncate. Margin: Entire; distally, sparsely and shallowly serrate; coarsely undulate. Color, upper surface: Close to a blend of NN137A and 139A; towards the margins, tinged with close to 183A. Color, lower surface: Close to 138A; towards the margins, tinged close to N186C.

*Peduncles*.—Length: About 37.1 cm. Diameter: About 8 mm to 9 mm. Aspect: About 25° from vertical. Strength: Strong. Texture and luster: Smooth, glabrous; moderately glossy. Color: Close to 144C and heavily covered with fine dots, close to 183A.

*Pedicels*.—Length: About 4.7 cm. Diameter: About 4 mm. Aspect: About 10° from peduncle axis. Strength: Moderately strong. Texture and luster: Smooth, glabrous; moderately glossy. Color: Close to 144C and heavily covered with fine dots, close to 185A.

*Reproductive organs*.—Stamens: Quantity per flower: About 100. Filament length: About 1.5 cm. Filament color: Close to NN155D. Anther shape: Double and broadly reniform; basifixed. Anther size: About 1.75 mm by 2.5 mm. Anther color: Close to 150C. Pollen amount: Sparse to moderate. Pollen color: Close to 4D. Pistils: Quantity per flower: About seven. Pistil length: About 1 cm. Stigma diameter: About 0.3 mm. Stigma shape: Club-shaped. Stigma color: Close to 157D. Style length: About 9 mm. Style color: Close to 187A. Ovary color: Close to 150D. Nectaries (transformed petals): Quantity per flower: About 13 to 18. Length: About 1.35 cm. Diameter: About 4.5 mm. Shape: Tubular, flattened; apices, obtuse. Texture and luster, inner and outer surfaces: Smooth, glabrous; slightly glossy. Color, immature, inner surface: Close to 145A to 145B; towards the apex, close to 145C; towards the base, close to 151A. Color, immature, outer surface: Close to 145B; towards the base, close to 146D and at the base, close to 178A. Color, mature, inner surface: Close to 145A to 145B; at the apex, close to 145C; towards the base, close to 152C to 152D; venation, similar to lamina colors; with subsequent development, color becoming closer to 151A with close to 153D at the apex and at the base, close to 153A to 153B. Color, mature, outer surface: Close to a blend of 144A and 146D; towards the base, close to 178A; venation, similar to lamina colors; with subsequent development, color becoming closer to 146D with close to 153C to 153D at the apex and at the base, close to 165B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1010' as illustrated and described.

* * * * *